(12) United States Patent
Mimura

(10) Patent No.: US 7,654,670 B2
(45) Date of Patent: Feb. 2, 2010

(54) ELECTRIC JOYSTICK MECHANISM FOR AN OPHTHALMIC APPARATUS

(75) Inventor: Yoshiaki Mimura, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 12/230,507

(22) Filed: Aug. 29, 2008

(65) Prior Publication Data

US 2009/0079939 A1 Mar. 26, 2009

(30) Foreign Application Priority Data

Sep. 3, 2007 (JP) ............................. 2007-228345

(51) Int. Cl.
*A61B 3/14* (2006.01)
(52) U.S. Cl. ...................... 351/208; 351/245
(58) Field of Classification Search ................ 351/205, 351/208, 210, 211, 245
See application file for complete search history.

(56) References Cited

U.S. PATENT DOCUMENTS

| | | | |
|---|---|---|---|
| 5,352,889 A | 10/1994 | Fujieda et al. | |
| 5,406,076 A | 4/1995 | Mimura et al. | |
| 5,500,696 A | 3/1996 | Masuda et al. | |
| 5,589,899 A * | 12/1996 | Maeda et al. | ............... 351/245 |
| 5,644,375 A * | 7/1997 | Suzuki | ...................... 351/208 |

FOREIGN PATENT DOCUMENTS

| | | |
|---|---|---|
| JP | A-06-007292 | 1/1994 |
| JP | A-06-014882 | 1/1994 |
| JP | A-06-046999 | 2/1994 |
| JP | A-07-016204 | 1/1995 |
| JP | A-2002-010979 | 1/2002 |
| JP | A-2002-369799 | 12/2002 |
| JP | A-2003-210404 | 7/2003 |

* cited by examiner

*Primary Examiner*—Huy K Mai
(74) *Attorney, Agent, or Firm*—Oliff & Berridge, PLC

(57) ABSTRACT

An electric joystick mechanism for an ophthalmic apparatus which is capable of improving manipulation performance of a joystick and is simple in structure comprises a base, a joystick having a shaft, a driving unit having a motor for moving an ophthalmic examination unit horizontally, and a control unit for controlling the driving unit in response to tilting manipulation of the joystick by an examiner, wherein the control unit performs first control of finely moving the examination unit by controlling the driving unit based on a manipulation signal of the joystick, and second control of roughly moving the examination unit by controlling the driving unit when tilting condition of the joystick becomes a predetermined tilting condition, and in the second control, velocity of driving of the driving unit is controlled based on velocity of the tilting manipulation of the joystick in the first control.

8 Claims, 4 Drawing Sheets

ELECTRIC JOYSTICK MECHANISM FOR AN OPHTHALMIC APPARATUS

BACKGROUND OF THE INVENTION

1. Field of the Invention

The present invention relates to an electric joystick mechanism for an ophthalmic apparatus, which moves an ophthalmic examination unit horizontally.

2. Description of Related Art

In recent years, in an ophthalmic apparatus which requires alignment with respect to an examinee's eye (e.g., an auto refractometer, a fundus camera), such an apparatus that electrically detects manipulation of a joystick and a trackball by an examiner and electrically drives an ophthalmic examination unit having a measurement optical system and other elements based on a result of the detection is proposed (see Japanese Patent Application Unexamined Publication No. 2002-369799).

In the apparatus disclosed in Japanese Patent Application Unexamined Publication No. 2002-369799, driving and control of the examination unit is divided into positional control and velocity control in accordance with a tilting angle of the joystick. In addition, a technique of controlling the examination unit so that movement velocity increases with an increase of the tilting angle in a range of the tilting angle of the joystick (e.g., 20 degrees to 35 degrees) which is beyond a predetermined angle.

The joystick mechanism disclosed in Japanese Patent Application Unexamined Publication No. 2002-369799 is provided with a first rotation shaft which rotates together with tilting movement of the joystick in a back/forth direction, a first potentiometer which detects a rotation angle of the first rotation shaft, a second rotation shaft which rotates together with tilting movement of the joystick in a right/left direction and a second potentiometer which detects a rotation angle of the second rotation shaft, and is arranged to electrically detect the manipulation of the joystick by the examiner by converting the tilting movement of the joystick into rotation movement of the rotation shafts in the back/forth direction and in the right/left direction.

The above-described electric joystick mechanism is desired to reflect an intention of the examiner and to have high operability. However, in the apparatus disclosed in Japanese Patent Application Unexamined Publication No. 2002-369799, fine angle adjustment of the joystick is difficult to be performed, and the examination unit could unintentionally move at a speed which is against the examiner's intention when the velocity control is performed in the range of the tilting angle of the joystick which is beyond the predetermined angle. In addition, it is necessary to largely tilt (e.g., at 35 degrees) the joystick in order to move the examination unit quickly, which takes time and effort for the examiner. In addition, the joystick mechanism disclosed in Japanese Patent Application Unexamined Publication No. 2002-369799 is complicated in structure as a whole because the rotation shafts which are different in shape need to be prepared (in the vicinities of connections with the joystick) in order to convert the tilting movement of the joystick into the rotation movement of the rotation shafts in the back/forth direction and in the right/left direction.

SUMMARY OF THE INVENTION

An object of the invention is to overcome the problems described above and to provide an ophthalmic apparatus comprising an electric joystick mechanism which is capable of improving manipulation performance of a joystick, and is simple in structure.

To achieve the objects and in accordance with the purpose of the present invention, an electric joystick mechanism which moves an ophthalmic examination unit horizontally, the mechanism comprises a base, a joystick having a shaft, which is supported so as to be tiltable in back/forth and right/left directions with respect to the base, a driving unit having a motor, which is arranged to move the examination unit horizontally, and a control unit which is arranged to control the driving unit in response to tilting manipulation of the joystick by an examiner, wherein the control unit performs first control of finely moving the examination unit by controlling the driving unit based on a manipulation signal of the joystick which is sequentially inputted in accordance with variance of tilting condition of the joystick, and second control of roughly moving the examination unit by controlling the driving unit when the tilting condition of the joystick becomes a predetermined tilting condition, and in the second control, velocity of driving of the driving unit is controlled based on velocity of the tilting manipulation of the joystick in the first control.

Additional objects and advantages of the invention are set forth in the description which follows, are obvious from the description, or may be learned by practicing the invention. The objects and advantages of the invention may be realized and attained by the electric joystick mechanism for an ophthalmic apparatus in the claims.

BRIEF DESCRIPTION OF THE DRAWINGS

The accompanying drawings, which are incorporated in and constitute a part of this specification, illustrate an embodiment of the present invention and, together with the description, serve to explain the objects, advantages and principles of the invention. In the drawings.

DETAILED DESCRIPTION OF THE PREFERRED EMBODIMENTS

Figure 1:
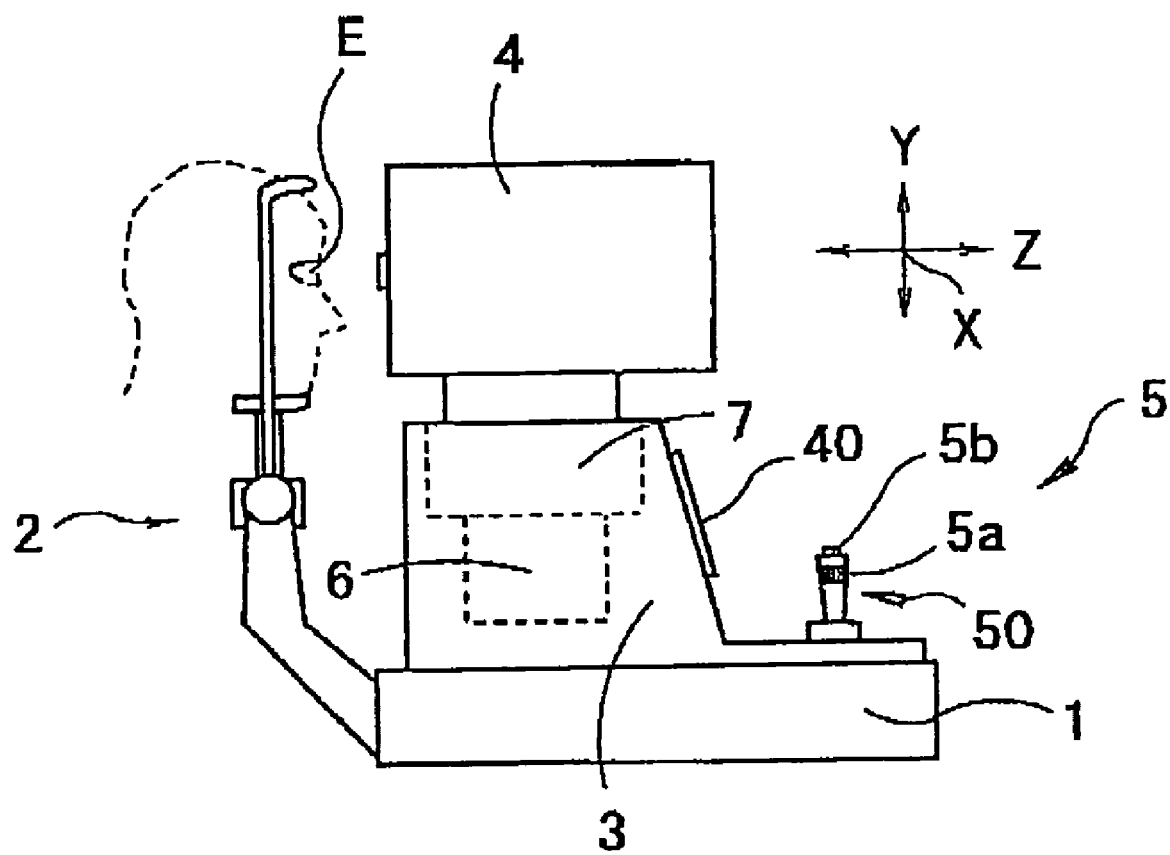
FIG. 1 is a schematic external view showing an ophthalmic apparatus comprising a joystick mechanism according to a preferred embodiment of the present invention.

A detailed description of an electric joystick mechanism for an ophthalmic apparatus according to a preferred embodiment of the present invention is provided below with reference to the accompanying drawings. FIG. 1 is a schematic external view showing the ophthalmic apparatus comprising the joystick mechanism according to the preferred embodiment of the present invention. The ophthalmic apparatus is a stationary ophthalmic apparatus comprising a base 1, a face supporting unit 2 attached to the base 1, main body 3 mounted on the base 1, a measurement unit (an ophthalmic examination unit) 4 which houses a measurement optical system (e.g., an eye refractive power measurement optical system) arranged to examine an examinee's eye E, and a joystick mechanism 5 which is operated in order to move the measurement unit 4.

The measurement unit 4 is moved in an up/down direction (a Y-direction shown in FIG. 1) with respect to the eye E by a Y driving unit 6 provided in the main body 3. In addition, the measurement unit 4 is moved in a right/left direction (an X-direction) and in a back/forth (working distance) direction (a Z-direction) with respect to the eye E by an XZ driving unit 7 provided on the Y driving unit 6. In this case, the XZ driving unit 7 has a large driving range which is secured so that alignment of the measurement unit 4 is performed with respect to right and left eyes of the examinee.

Figure 2A:
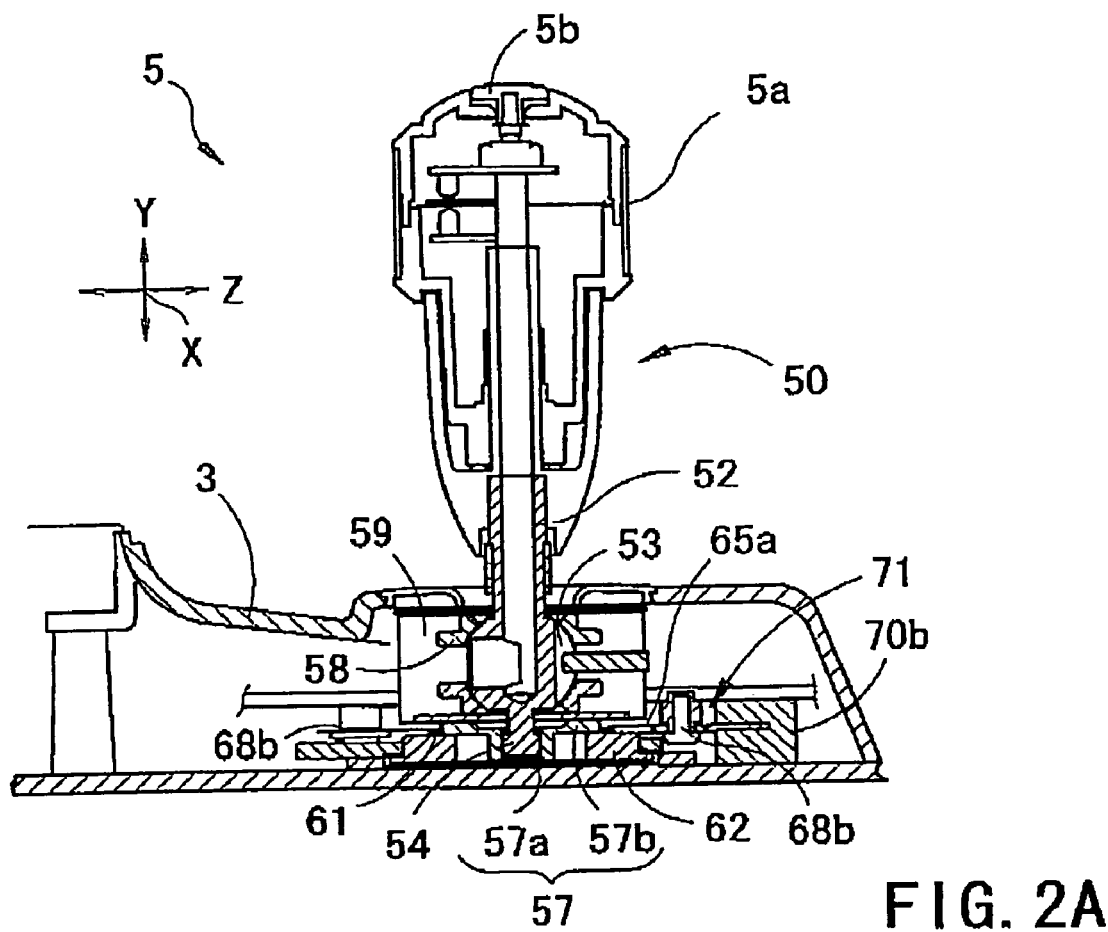
FIGS. 2A and 2B are views for illustrating the joystick mechanism according to the preferred embodiment of the present invention.
Figure 2B:
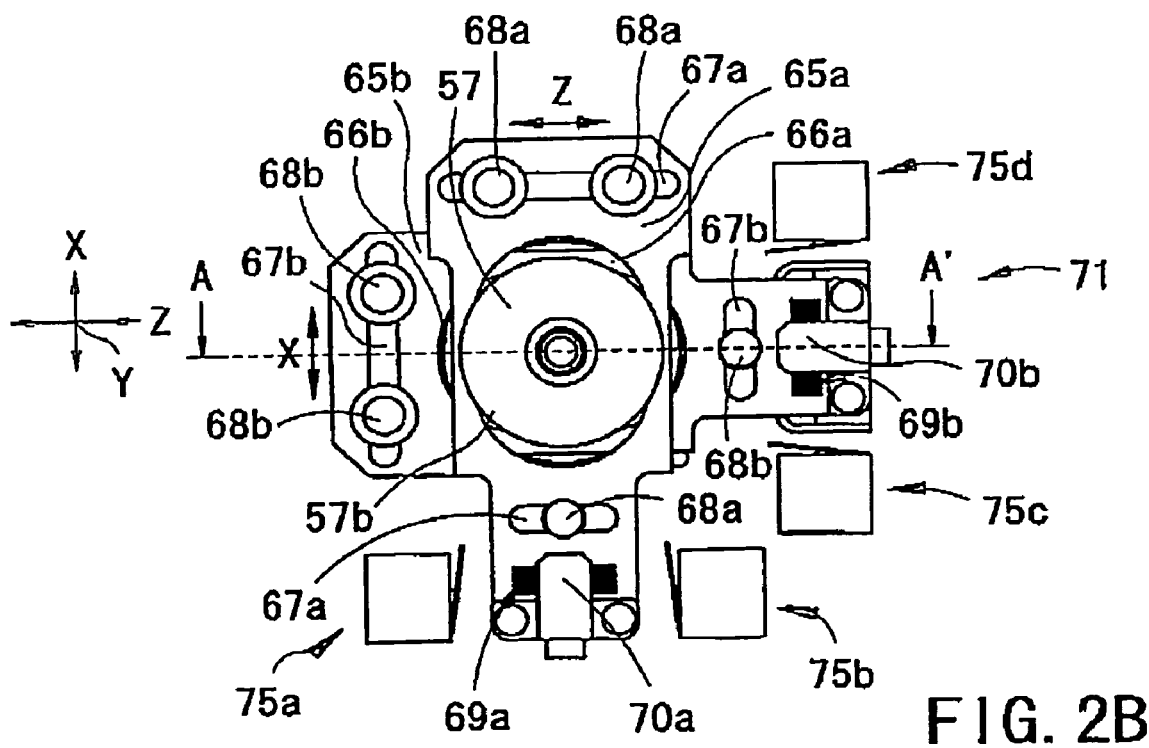

As shown in FIGS. 2A and 2B, the joystick mechanism 5 comprises a joystick 50 which is manipulated in order to move the measurement unit 4, a supporting unit 59 which supports the joystick 50 so as to be tiltable in an arbitrary direction, a movement member 57 placed below the joystick 50, which is moved horizontally in synchronization with the tilting manipulation of the joystick 50, a movement detecting unit 71 which detects the horizontal movement of the movement member 57 and outputs a detection signal. To be more specific, the tilting manipulation of the joystick 50 by an examiner is electrically detected, and the XZ driving unit 7 is driven based on the detection signal from the joystick mechanism 5. Accordingly, when the examiner manipulates the joystick 50, the measurement unit 4 is moved in the horizontal direction (the X-direction and the Z-direction) by the driving of the XZ driving unit 7. When the examiner rotates and manipulates a rotation knob 5a, the measurement unit 4 is moved in the Y-direction by the driving of the Y driving unit 6. A measurement starting switch 5b is provided at the top of the joystick 50. The main body 3 is provided with a display monitor 40.

FIGS. 2A and 2B are views for illustrating the joystick mechanism 5 according to the preferred embodiment of the present invention. FIG. 2A is a lateral sectional view of the joystick mechanism, and FIG. 2B is a schematic view showing relevant parts of the joystick mechanism shown in FIG. 2A, which is seen from downward.

As shown in FIG. 2A, a shaft 52 is inserted through the joystick 50, and below the shaft 52, a spherical portion 53 which is supported by a ball bearing 58 included in the supporting unit 59 and a spherical portion 54 in a substantially spherical shape which is engaged with a cylindrical vessel portion (a concave portion) 57a of the movement member 57 are provided. The rotation knob 5a which rotates about the shaft 52 is provided at an upper portion of the joystick 50. The supporting unit 59 is fixed in a housing of the main body 3 fixed to the base 1.

The movement member 57 is placed between a first sliding member 61 having the shape of a doughnut which is fixed to the supporting unit 59 and a second sliding member 62 having the shape of a doughnut which is provided on the bottom of the main body 3 so as to be slidable in the horizontal direction. The second sliding member 62 comprises an elastic member (not shown) such as a spring inside thereof and presses the movement member 57 upward with an elastic force of the elastic member. With a structure like this, a tilting state of the joystick 50 can be maintained when the joystick 50 is manipulated. Meanwhile, when the examiner applies an arbitrary force to the joystick 50, the movement member 57 is moved in the horizontal direction against a pressing force of the second sliding member 62 and the joystick 50 is tilted. Therefore, manipulation feeling of the joystick mechanism 5 according to the preferred embodiment of the present invention is similar to manipulation feeling of a mechanical (manual) joystick mechanism which moves the measurement unit 4 by mechanically sliding the measurement unit 4 and the main body 3 with respect to the base 1.

The movement detecting unit 71 comprises guide plates 65a and 65b, and sensors 70a and 70b. The guide plates 65a and 65b made of a thin flat plate are engaged with peripheral portions of a flange 57b which is provided at an upper portion of the movement member 57 so as to intersect at right angles with each other. In this case, the guide plates 65a and 65b are respectively provided with oval holes 66a and 66b which intersect at right angles with each other. The guide plates 65a and 65b are placed so that movement directions of the guide plates 65a and 65b coincide respectively with the directions of shorter diameters of the oval holes 66a and 66b, and portions of the shorter diameters of the oval holes 66a and 66b are respectively engaged with the peripheral portions of the flange 57b of the movement member 57. By having such a structure, the guide plates 65a and 65b are moved in the respective directions by the movement of the movement member 57 in the horizontal direction. The lengths of longer diameters of the oval holes 66a and 66b which intersect with the shorter diameters are determined so that the peripheral portions of the flange 57b of the movement member 57 do not interfere (are not engaged) with other portions of the guide plates 65a and 65b. To be specific, a pair of hollow spaces (substantially in a crescent shape) 66a are formed right and left in a direction perpendicular to the movement direction of the guide plate 65a between the peripheral portions of the flange 57b and the oval hole 66a, and a pair of hollow spaces (substantially in a crescent shape) 66b are formed back and forth in a direction perpendicular to the movement direction of the guide plate 65b between the peripheral portions of the flange 57b and the oval hole 66b, whereby the guide plates 65a and 65b are arranged to be movable independently in the respective directions.

The guide plate 65a is provided with two slits (guide holes) 67a extending in the back/forth direction, and is accordingly arranged to be slidable in the back/forth direction by limiting the movement direction by rollers (guide shafts) 68a fixed in the housing of the main body 3. The guide plate 65b is provided with two slits (guide holes) 67b extending in the right/left direction, and is arranged to be slidable in the right/left direction by limiting the movement direction by rollers (guide shafts) 68b fixed in the housing of the main body 3.

The guide plates 65a and 65b are respectively provided with slits 69a and 69b for detection in each of which minute slits are given at equal spaces, so that a movement direction, a movement amount, movement velocity and other information of the movement member 57 can be detected by the sensors (e.g., an optical encoder, a magnetic encoder) 70a and 70b fixed in the housing of the main body 3. As a specific configuration of the sensor 70a (70b), a configuration is conceivable in which two photointerrupters are placed side by side in a movement direction of the slits so that phases of square waves (pulse signals) to be outputted therefrom mutually differ in pitch by a quarter. In this case, by detecting a relation of the phases, the number of the pulses, time intervals between, and other data of the pulse signals which are outputted from the two photointerrupters, the movement direction, the movement amount and the movement velocity of the movement member 57 are detected. Detection signals outputted from the sensors 70a and 70b are inputted to a control unit 80. The control unit 80 drives and controls the XZ driving unit 7 based on the detection signals from the sensors 70a and 70b to move the measurement unit 4 in the X- and Z-directions. In this case, the sensors 70a and 70b are used in order to detect the tilting movement of the joystick 50 which is manipulated in a range where the joystick 50 is not tilted up to a predetermined tilting limit position.

In addition, the joystick mechanism 5 is provided with four detection units 75a to 75d for detecting that the joystick 50 is tilted up to the predetermined tilting limit position. The detection units 75a and 75b are placed so as to sandwich the guide plate 65a therebetween in the back/forth direction. The detection units 75c and 75d are placed so as to sandwich the guide plate 65b therebetween in the right/left direction. The detection units 75a to 75d are preferably made from microswitches, and detect that the joystick 50 is tilted up to the predetermined tilting limit position when edge faces of the guide plates 65a and 65b come into contact with the detection units 75a to 75d.

Figure 3:
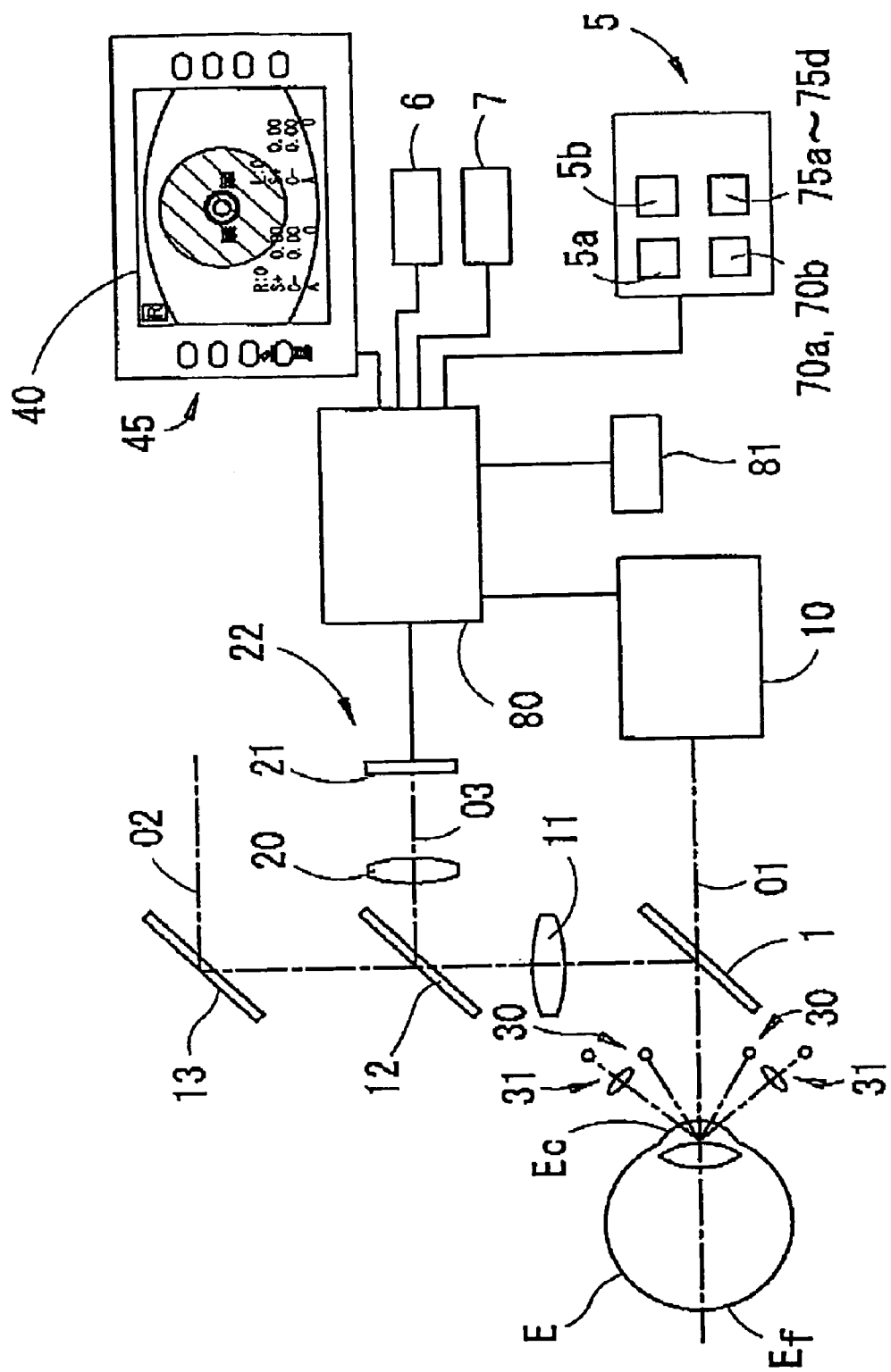
FIG. 3 is a view showing a schematic configuration of an optical system and a control system of the ophthalmic apparatus comprising the joystick mechanism according to the preferred embodiment of the present invention.

FIG. 3 is a view showing a schematic configuration of an optical system and a control system of the ophthalmic apparatus comprising the joystick mechanism according to the preferred embodiment of the present invention. A measurement optical system 10 is placed on a transmission optical path O1 of a dichroic mirror 1 which is placed in front of the eye E. An objective lens 11, a dichroic mirror 12 and a total reflection mirror 13 which are used for observing the eye E are placed in a reflecting direction of the dichroic mirror 1. A fixation target projection optical system (not shown) for making the eye E fixate a fixation target is placed on an optical path O2 in a reflecting direction of the total reflection mirror 13. An observation optical system 22 comprising an image forming lens 20 and a two-dimensional photo-receiving element 21 such as an area CCD placed in a position almost conjugate with the vicinity of an anterior segment of the eye E, for photographing the eye E and obtaining an image of the eye E is placed on an optical path O3 in a reflecting direction of the dichroic mirror 12.

A ring target projection optical system 30 for emitting near infrared light for projecting a ring target onto a cornea Ec of the eye E, and a target projection optical system 31 for working distance detection, for emitting near infrared light for detecting an alignment state of the measurement unit 4 in the working distance direction with respect to the eye E by projecting an infinite target onto the cornea Ec are placed in front of the anterior segment of the eye E and symmetrically with respect to an observation optical axis. The ring projection optical system 30 is used also as an anterior-segment illumination which illuminates the anterior segment of the eye E.

The dichroic mirror 1 has a property of transmitting light emitted from a measurement light source included in the measurement optical system 10 and reflecting light emitted from the ring target projection optical system 30 and light emitted from the target projection optical system 31 for working distance detection and visible light. The dichroic mirror 12 has a property of transmitting visible light and reflecting infrared light.

The control unit 80 performs calculation for obtaining eye refractive power based on an output signal from the measurement optical system 10, drives and controls the XZ driving unit 7 and Y driving unit 6 based on output signals from the joystick mechanism 5, and controls the apparatus as a whole. An image signal from the image-pickup element 21 is inputted to the control unit 80. An image of the anterior segment obtained by the image-pickup element 21, and a measurement result and display information such as a mark for alignment are superimposed (overlapped), and then are displayed on a display screen of the display monitor 40. The control unit 80 is connected with a memory 81 which stores data including the measurement result, the joystick mechanism 5, the XZ driving unit 7, the Y driving unit 6, an operation switch unit 45 for performing various kinds of setting concerning examinations (e.g., switching of a measurement mode, switching of an alignment mode) and other elements.

The operation of the apparatus having the above-described structure is described. The examiner fixes a face of the examinee to the face supporting unit 2 and performs alignment with the eye E. The examiner moves the measurement unit 4 three-dimensionally and performs positional adjustment of the measurement unit 4 by tilting the joystick 50 and rotating the rotation knob 5a while observing the display monitor 40, and performs rough alignment so that the anterior-segment image of the eye E appears in the display screen of the display monitor 40. The examiner tilts the joystick 50 in the back/forth and right/left directions in order to move the measurement unit 4 in the back/forth and right/left directions with respect to the eye E. In addition, the examiner rotates the rotation knob 5a in order to move the measurement unit 4 in the up/down direction with respect to the eye E.

If the eye E is positioned far from the measurement unit 4, the examiner tilts the joystick 50 up to the limit position in order to quickly move the measurement unit 4 toward the eye E. When the joystick 50 is tilted up to the limit position in a predetermined direction, one of the detection units 75a to 75d which is placed in the direction opposite to the predetermined direction is pressed against the edge faces of the guide plates 65a and 65b. In this case, the detection units 75a to 75d output detection signals to the control unit 80 in accordance with the tilting direction of the joystick 50. For example, when the joystick 50 is tilted left, the detection unit 75c outputs the detection signal to the control unit 80.

Then, the control unit 80 obtains the tilting direction of the joystick 50 based on the detection signals from the detection units 75a to 75d, and drives the XZ driving unit 7 to move the measurement unit 4 in the direction corresponding to the tilting direction (rough movement control). For example, when the joystick 50 is tilted in the left direction, the control unit 80 controls the measurement unit 4 to move in the left direction. When the joystick 50 is tilted in a left anterior oblique direction, the control unit 80 controls the measurement unit 4 to move in the left anterior oblique direction. In the present preferred embodiment of the present invention, when the measurement unit 4 is moved in response to the detection signals from the detection units 75a to 75d, the control unit 80 drives the XZ driving unit 7 at high speed to move the measurement unit 4 quickly. Accordingly, the measurement unit 4 is moved at high speed in the tilting direction of the joystick 50, which allows prompt positional adjustment.

As described above, when the anterior-segment image appears on the display monitor 40 and the alignment of the measurement unit 4 with respect to the eye E is completed to some extent, the examiner stops the high-speed movement of the measurement unit 4 by manipulating the joystick 50 in the direction opposite to the direction where the joystick 50 reaches the tilting limit position. At this time, a state where the detection units 75a to 75d are pressed against the guide plates 65a and 65b is released, whereby the detection units 75a to 75d stop outputting the detection signals to the control unit 80. The control unit 80 accordingly stops driving the XZ driving unit 7 to stop the movement of the measurement unit 4.

Figures 4A, 4B:
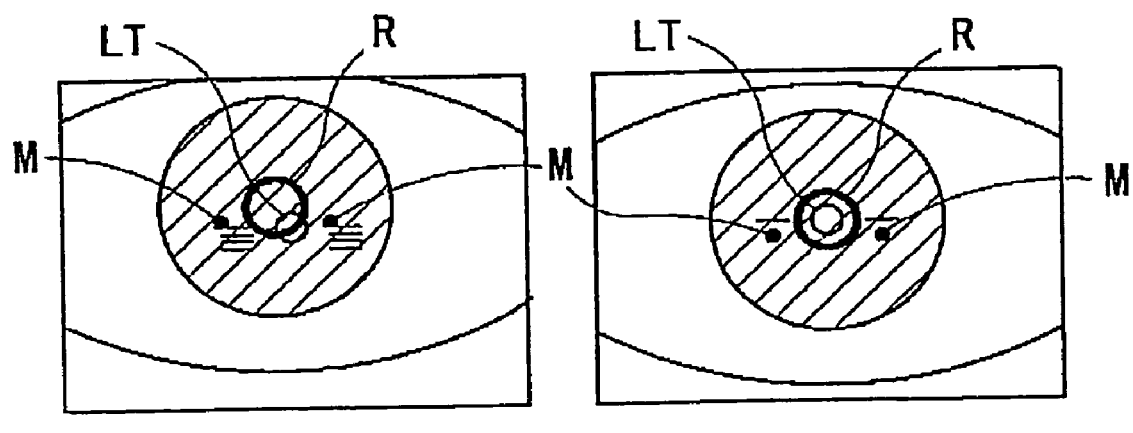
FIGS. 4A and 4B are views showing display screens for alignment displayed on a display monitor.

When the rough alignment is performed as described above, the anterior segment of the eye E is photographed by the image-pickup element 21, and the anterior-segment image, a reticle mark LT, a ring target image (a Mayer ring image) R projected by the ring projection optical system 30, an infinite target image M projected by the target projection optical system 31 for working distance detection and other images are displayed on the display monitor 40 (see FIG. 4A).

After instructing the examinee to fixate the fixation target (not shown), the examiner manipulates the joystick 50 while observing the ring target image (the Mayer ring image) R displayed on the display monitor 4 and adjusts the position of the measurement unit 4 in the up/down and right/left directions so that the ring target image R and the retile mark LT become concentric circles. Then, the examiner adjusts the position of the measurement unit 4 in the working distance direction with reference to an indicator (or so that the ring target image R becomes thinnest) (see FIG. 4B).

When the joystick 50 is pivoted (tilted) by the examiner, the shaft 52 is pivoted about the center of the spherical portion 53 via the ball bearing 58, and the spherical portion 54 provided below the joystick 50 is oscillated. Then, the movement member 57 engaged with the spherical portion 54 is moved in the direction opposite to the tilting direction of the joystick 50 and the guide plates 65a and 65b are moved in the horizontal direction. For example, when the joystick 50 is tilted in the forth direction, the guide plate 65a is moved in the back direction and when the joystick 50 is tilted in the left direction, the guide plate 65b is moved in the right direction.

The slits 69a and 69b for detection provided on the guide plates 65a and 65b are moved with respect to the sensors 70a and 70b, the detection signals from the sensors 70a and 70b are inputted to the control unit 80 as a pulse signals. In this case, the control unit 80 detects the movement velocity and the movement direction of the movement member 57 based on the inputted pulse signals. Hence, manipulation signals (manipulation velocity and a manipulation direction) of the joystick 50 are obtained. Then, the control unit 80 drives the XZ driving unit 7 based on the manipulation signals obtained based on the detection signal from the sensor 70a to move the measurement unit 4 in the back/forth direction (fine movement control). In this case, for example, when the joystick 50 is tilted in the forth direction and the guide plate 65a is moved in the back direction, the control unit 80 controls the measurement unit 4 to move in the forth direction. In addition, the control unit 80 drives the XZ driving unit 7 based on the manipulation signal obtained based on the detection signal from the sensor 70b to move the measurement unit 4 in the right/left direction (fine movement control). In this case, for example, when the joystick 50 is tilted in the left direction and the guide plate 65b is moved in the right direction, the control unit 80 controls the measurement unit 4 to move in the left direction.

Besides, in the present preferred embodiment of the present invention, the control unit 80 obtains the manipulation velocity of the joystick 50 in real time based on time intervals between the pulse signals (periods of time from detection of a pulse signal to detection of a next pulse signal) which are sequentially outputted from the sensors 70a and 70b. Then, the control unit 80 varies a voltage applied to a motor (e.g., a DC motor) provided to the XZ driving unit 7 based on the obtained manipulation velocity of the joystick 50, thereby controlling rotation velocity of the motor in real time. In this case, when the time intervals between the sequentially obtained pulse signals are shorter, the voltage applied to the motor becomes larger and the rotation velocity of the motor becomes faster, and when the time intervals between the sequentially obtained pulse signals are longer, the voltage applied to the motor becomes smaller and the rotation velocity of the motor becomes slower. Accordingly, the measurement unit 4 is moved largely when the joystick 50 is moved quickly, and the measurement unit 4 is moved finely when the joystick 50 is moved slowly. Therefore, when a relative distance between the eye E and the measurement unit 4 is shorter, the examiner performs fine adjustment of the alignment of the measurement unit 4 with respect to the eye E by manipulating the joystick 50 slowly.

In a case where the joystick 50 is left stopped at some midpoint without being tilted up to the tilting limit position (the detection signals are not outputted from the detection units 75a to 75d) and a next pulse signal is not detected more than a predetermined period of time since a pulse signal is detected, the control unit 80 judges that the tilting manipulation of the joystick 50 is terminated, and stops applying the voltage to the motor and stops the motor rotate. Accordingly, when the examiner terminates the tilting manipulation of the joystick 50, the movement of the measurement unit 4 in the horizontal direction is stopped. When the tilting movement of the joystick 50 is terminated (the force to move the joystick 50 exerted by the examiner is released) the joystick 50 is brought to a state where the joystick 50 is held at a tilting angle at the time of termination of the tilting movement of the joystick 50 by an elastic force of the second sliding member 62. Thus, the movement velocity (the movement amount) of the measurement unit 4 is varied in accordance with the manipulation velocity of the joystick 50, whereby fine movement and rough movement of the measurement unit 4 can be performed with an manipulation feeling obtained similarly to the case of using the conventional mechanical joystick mechanism. When the fine movement manipulation of the measurement unit 4 with respect to the eye E using the joystick 50 is completed as described above and the measurement starting switch 5b is pressed by the examiner, measurement is performed. The control unit 80 actuates the measurement optical system 10 based on input of a trigger signal and performs the measurement of the eye E. After the completion of the measurement, a result of the measurement is displayed on the monitor 40.

The structure of the joystick mechanism 5 can be simplified by converting the tilting movement of the joystick 50 into the horizontal movement of the movement member 57 provided below the joystick 50 and detecting the movement of the movement member 57 in the horizontal direction as described above. In the above description, the joystick mechanism 5 is arranged so that the movement velocity of the movement member 57 is detected by the sensors 70a and 70b and the manipulation velocity of the joystick 50 is obtained; however, it is not limited thereto. For example, it is also preferable that the joystick mechanism 5 is arranged so that the movement amount of the movement member 57 is detected and the manipulation amount of the joystick 50 is obtained. It is also preferable that the joystick mechanism 5 is arranged so that a movement position of the movement member 57 is detected using a potentiometer or other detecting elements.

To be more specific, it is also preferable that the joystick mechanism 5 is arranged so that the manipulation amount of the joystick 50 and the movement amount of the measurement unit 4 have a relation in a pair (e.g., a proportional relation, a relation of a quadratic curve) by obtaining the manipulation velocity of the joystick 50 in real time based on the time intervals between the pulse signals sequentially outputted from the sensors 70a and 70b (or the number of pulses per predetermined period of time) and making the manipulation velocity correspond to the movement velocity of the measurement unit 4, and making the movement amount of the measurement unit 4 per pulse which is sequentially outputted from the sensors 70a and 70b constant. In this case, a pulse motor which is driven in response to the pulse signals outputted from the sensors 70a and 70b is preferably used as the motor used for the XZ driving unit 7. By this structure, even if the tilting velocity of the joystick 50 differs, the movement amounts of the measurement unit 4 are constant while the movement velocity of the measurement unit 4 is varied in accordance with the tilting velocity if the operation angles are the same. This allows the examiner to easily know the movement amount of the measurement unit 4 with respect to the manipulation amount of the joystick 50 and to perform precise alignment.

It is also preferable that automatic alignment to be described below is performed after the rough alignment is performed and the anterior segment of the eye E is photographed by the image-pickup element 21 as described above. Here, the control unit 80 detects an alignment state with respect to the eye E based on an image-pickup signal from the image-pickup element 21. In this case, the control unit 80 obtains the alignment state in the up/down and right/left directions with respect to the eye E, for example, based on central coordinates of the ring target R. In addition, the control unit 80 obtains an alignment state in the working distance direction with respect to the eye E by making use of a property that a space of the ring target image R in a predetermined meridian direction vary while a space between the infinite target images M vary little when the measurement unit 4 deviates in the working distance direction (see Japanese Patent Application Unexamined Publication No. Hei06-46999). Then, based on a detection result of the alignment, the control unit 80 drives and controls the Y driving unit 6 and the XZ driving unit 7 to move the measurement unit 4, and performs the automatic alignment with the eye E. After the completion of the alignment, the control unit 80 automatically emits a trigger signal and starts the measurement (auto shot).

The apparatus having a function of the automatic alignment as described above allows the automatic alignment using the automatic alignment function to be performed on an examinee's eye for which the automatic alignment is effective and the manual alignment using the joystick mechanism 5 to be performed on an examinee's eye for which the automatic alignment is not effective (e.g., an eye with abnormality in a cornea, an eye with rapid involuntary fine movement).

While the control unit 80 is arranged to drive the XZ driving unit 7 at high speed in driving and controlling the XZ driving unit 7 to perform the rough movement of the measurement unit 4 based on the detection signals from the detection units 75*a* to 75*d*, the control unit 80 may be arranged to vary the velocity at which the measurement unit 4 is roughly moved based on the manipulation velocity of the joystick 50 obtained when the joystick 50 is tilted.

In this case, when the joystick 50 is tilted by the examiner, the control unit 80 sequentially obtains the manipulation velocity of the joystick 50 based on the detection signals from the sensors 70*a* and 70*b*, and drives the XZ driving unit 7 based on the obtained manipulation velocity (a fine-movement manipulation mode) as described above. When the joystick 50 is tilted up to the limit position in the predetermined direction, the control unit 80 drives the XZ driving unit 7 based on the detection signals from the detection units 75*a* to 75*d* (a rough-movement manipulation mode). In the rough-movement manipulation mode, the control unit 80 obtains the manipulation velocity of the joystick 50 based on the detection signals outputted from the sensors 70*a* and 70*b* for a period of time when the joystick 50 is tilted by the examiner, and controls driving velocity of the XZ driving unit 7 based on the obtained manipulation velocity.

Hence, at the stage before the detection signals from the detection units 75*a* to 75*d* are outputted, the velocity at which the measurement unit 4 is roughly moved becomes higher when the manipulation velocity of the joystick 50 is higher, and the velocity at which the measurement unit 4 is roughly moved becomes lower if the manipulation velocity of the joystick 50 is lower. That is to say, the velocity at which the measurement unit 4 is roughly moved varies based on the manipulation velocity of the joystick 50 in the fine movement control. To be specific, since it is conceivable that the examiner intends to move the measurement unit 4 largely (e.g., in a case where switching between the right eye and the left eye is performed) when the joystick 50 is tilted quickly, the movement unit 4 is moved largely by moving the measurement unit 4 quickly. In addition, since it is conceivable that the examiner intends to move the measurement unit 4 finely (e.g., in a case where the alignment with the eye is to be completed if the measurement unit 4 moves a little more while the eye is positioned outside a movable range of the measurement unit 4 moved by the fine-movement manipulation of the joystick 50 (the movement of the measurement unit 4 in response to the detection signals from the sensors 70*a* and 70*b*) when the joystick 50 is tilted slowly, the measurement unit 4 is moved finely by moving the measurement unit 4 slowly.

This allows the examiner to perform movement of the measurement unit 4 which reflects the intention of the examiner who manipulates the joystick 50 also in the rough-movement manipulation in addition to the fine-movement manipulation.

In the above-described control, the control unit 80 controls the driving velocity of the XZ driving unit 7 based on the manipulation velocity of the joystick 50 obtained just before the detection signals from the detection units 75*a* to 75*d* are outputted. Then, the control unit 80 drives and controls the XZ driving unit 7 to maintain its driving velocity so that the movement velocity of the measurement unit 4 just before the detection signals from the detection units 75*a* to 75*d* are outputted becomes equal to the movement velocity of the measurement unit 4 in the rough-movement manipulation (when the detection signals from the detection units 75*a* to 75*d* are outputted). Hence, the rough movement of the measurement unit 4 is performed while the movement velocity of the measurement unit 4 in the fine-movement manipulation mode is maintained. Accordingly, even when the rough-movement manipulation mode (a state where the joystick 50 reaches the predetermined tilting limit position) is switched from the fine-movement manipulation mode, the examiner can manipulate the joystick 50 as if the fine-movement manipulation mode (the state where the joystick 50 is not tilted up to the predetermined tilting limit position) were kept without being bothered by a feeling of strangeness.

In the above description, it is arranged that the rough movement of the measurement unit 4 is performed based on the manipulation velocity of the joystick 50 obtained just before the detection signals from the detection units 75*a* to 75*d* are outputted; however, it is not limited thereto. For example, it is also preferable that the control unit 80 controls the driving velocity of the XZ driving unit 7 based on an average value of the manipulation velocity of the joystick 50 for a predetermined period of time from when the joystick 50 is tilted till when the joystick 50 reaches the tilting limit position (e.g., for one second before the detection signals from the detection units 75*a* to 75*d* are outputted).

In the apparatus in which the rough-movement manipulation of the measurement unit 4 with respect to the eye can be performed as described above, it is also preferable to provide a velocity adjustment switch for adjusting (increasing/decreasing) the movement velocity of the measurement unit 4 with respect to the eye in the rough-movement manipulation and to control the movement velocity of the measurement unit 4 based on a switch signal by the velocity adjustment switch. For example, when roughly driving the XZ driving unit 7 based on the detection signals from the detection units 75a to 75d as described above, the control unit 80 increases and decreases the driving velocity of the XZ driving unit 7 in response to input of the switch signals by the velocity adjustment switch. It is preferable that the velocity adjustment switch is placed in the vicinity of the joystick 50. For example, it is preferable that a function of the velocity adjustment switch is added to the measurement starting switch 5b and is used in combination therewith. In this case, when the detection signals from the detection units 75a to 75d are outputted, the control unit 80 rejects the trigger signal for starting the measurement operation so that the measurement operation is not performed in the rough-movement manipulation.

In the above-described joystick mechanism 5, it is also preferable that a rough movement switch for performing the rough movement of the measurement unit 4 with respect to the eye is provided and the control unit 80 drives and controls the XZ driving unit 7 based on the detection signals from the detection units 75a to 75d in response to a trigger signal inputted to the control unit 80 by the rough movement switch. In this case, the control unit 80 does not drive and control the XZ driving unit 7 unless the trigger signal is inputted by the rough movement switch to the control unit 80 even if the detection signals from the detection units 75a to 75d are inputted thereto. When the detection signals from the detection units 75a to 75d are inputted to the control unit 80 and the trigger signal by the rough movement switch is inputted thereto, the control unit 80 drives and controls the XZ driving unit 7 based on the detection signals from the detection units 75a to 75d. Then, the control unit 80 keeps driving and controlling the XZ driving unit 7 until the trigger signal by the rough movement switch is cancelled or the detection signals from the detection units 75a to 75d are not outputted any more.

This can prevent the rough movement of the measurement unit 4 from being performed against the examiner's intention, which is caused by the tilting of the joystick 50 to the predetermined limit position during the time when the examiner performs the fine movement of the measurement unit 4 (the movement of the measurement unit 4 based on the detection signals from the sensors 70a and 70b) with respect to the eye. When the above-described rough movement switch is provided, it is also preferable, contrary to the above-described case, that the control unit 80 does not drive and control the XZ driving unit 7 as long as the trigger signal by the rough movement switch is inputted to the control unit 80 even if the detection signals from the detection units 75a to 75d are inputted thereto. Here, the control unit 80 drives the XZ driving unit 7 based on the detection signals from the detection units 75a to 75d when the detection signals from the detection units 75a to 75d are inputted to the control unit 80 and the trigger signal by the rough movement switch is cancelled. Then, the control unit 80 keeps driving and controlling the XZ driving unit 7 until the trigger signal by the rough movement switch is emitted or the detection signals from the detection units 75a to 75d are not outputted any more. In this case, it is essential only that the rough movement switch be not turned on when performing the rough movement and that the rough movement switch be turned on when prohibiting the rough movement. Besides, in the above-described driving operation, it is also preferable that the rough movement switch is used only as a trigger switch for starting the rough movement and the rough movement is stopped in response to the extinction of the detection signals from the detection units 75a to 75d.

It is preferable that the rough movement switch is provided in the vicinity of the joystick 50, and it is preferable that a function of the rough movement switch is added to the measurement starting switch 5b and is used in combination. In this case, when the detection signals from the detection units 75a to 75d are inputted to the control unit 80, the control unit 80 rejects the trigger signal for starting the measurement operation so that the measurement operation is not performed in the rough-movement manipulation.

In a case where the alignment state of the measurement unit 4 with respect to the eye is detectable as described above, the control unit 80 restricts the movement of the measurement unit 4 based on the detection signals from the detection units 75a to 75d under certain conditions in accordance with the detected alignment state. To be more specific, the control unit 80 does not drive the XZ driving unit 7 when an alignment deviation amount of the measurement unit 4 with respect to the eye which is detected based on the image-pickup signal from the image-pickup element 21 falls within a predetermined permissible range (e.g., within a range where the measurement unit 4 can be moved through the tilting manipulation of the joystick 50 performed in a range where the detection signals from the detection units 75a to 75d are not outputted) even if the detection signals from the detection units 75a to 75d are outputted. Hence, the rough movement of the measurement unit 4 against the examiner's intention can be avoided without the above-described switch operation.

In a case where the above-described rough movement switch is provided, when the detection signals from the detection units 75a to 75d are not outputted any more, the alignment mode is switched from the rough-movement manipulation mode to the fine-movement manipulation mode. It is also preferable that the control unit 80 stops the driving and control of the XZ driving unit 7 based on the detection signals from the sensors 70a and 70b until the trigger signal inputted by the rough movement switch is cancelled even if the detection signals from the detection units 75a to 75d are not outputted any more. In this case, the examiner performs the rough movement of the measurement unit 4 as described above, returns the joystick 50 to a neutral position (an upright position) while keeping the rough movement switch pressed, and then releases the input by the rough movement switch. When the trigger signal by the rough movement switch are not outputted any more, the control unit 80 restarts the driving and control of the XZ driving unit 7 which is based on the detection signals from the sensors 70a and 70b, which allows the fine movement to be performed by the examiner. Hence, the movement of the measurement unit 4 is stopped for a period of time from when the joystick 50 is tilted to the predetermined limit position till when the joystick 50 is returned to the vicinity of the neutral position from the predetermined tilting limit position. Accordingly, the fine movement can be started smoothly since the fine movement can be performed in a state where the joystick 50 is in the vicinity of the neutral position after the rough movement of the measurement unit 4 with respect to the eye is performed.

In the above description, it is arranged that the fine movement after the rough movement is restarted by the cancellation of the trigger signal by the rough movement switch; however, other techniques are conceivable. For example, it is also preferable to detect a manipulation amount of the joystick 50 from the tilting limit position, to judge whether or not the joystick 50 is returned to the vicinity of the neutral position based on a result of the detection, and to restart the fine movement based on a result of the judgment.

The operation of varying the velocity at which the measurement unit 4 is roughly moved based on the manipulation velocity of the joystick 50 in the fine-movement manipulation as described above is not limited to the joystick mechanism described above having the detection mechanism which detects the manipulation information (the manipulation velocity, the manipulation amount, manipulation position and other information) of the joystick 50 based on the movement of the movement member 57. The present invention is also applicable to another electric joystick mechanism having a detection mechanism which detects a tilting direction and a tilting angle of a joystick.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An electric joystick mechanism which moves an ophthalmic examination unit horizontally, the mechanism comprising:
   a base;
   a joystick having a shaft, which is supported so as to be tiltable in back/forth and right/left directions with respect to the base;
   a driving unit having a motor, which is arranged to move the examination unit horizontally; and
   a control unit which is arranged to control the driving unit in response to tilting manipulation of the joystick by an examiner,
   wherein the control unit performs first control of finely moving the examination unit by controlling the driving unit based on a manipulation signal of the joystick which is sequentially inputted in accordance with variance of tilting condition of the joystick, and second control of roughly moving the examination unit by controlling the driving unit when the tilting condition of the joystick becomes a predetermined tilting condition, and in the second control, velocity of driving of the driving unit is controlled based on velocity of the tilting manipulation of the joystick in the first control.

2. The electric joystick mechanism according to claim 1, wherein the control unit performs the second control so that velocity of the driving of the driving unit just before the tilting condition of the joystick becomes the predetermined tilting condition is equal to velocity of the driving of the driving unit after the tilting condition of the joystick becomes the predetermined tilting condition.

3. The electric joystick mechanism according to claim 1, further comprising an alignment detection optical system for detecting an alignment state of the examination unit with respect to an examinee's eye,
   wherein the second control is restricted in accordance with the alignment state detected by the alignment detection optical system.

4. The electric joystick mechanism according to claim 1, further comprising a rough movement switch which is arranged to initiate the rough movement of the examination unit with respect to an examinee's eye,
   wherein the control unit performs the second control when a signal is inputted by the rough movement switch.

5. The electric joystick mechanism according to claim 4, wherein the rough movement switch is an ophthalmic examination starting switch by which a trigger signal for starting ophthalmic examination by the examination unit is inputted, and the control unit rejects the trigger signal inputted by the staring switch when the tilting condition of the joystick becomes the predetermined tilting condition.

6. The electric joystick mechanism according to claim 1, further comprising a velocity adjustment switch which is arranged to adjust movement velocity of the examination unit with respect to an examinee's eye,
   wherein the control unit controls the velocity of the driving of the driving unit based on a signal inputted by the velocity adjustment switch.

7. The electric joystick mechanism according to claim 1, further comprising a movement member placed below the joystick, which is moved horizontally in synchronization with the tilting manipulation of the joystick,
   wherein the control unit detects the horizontal movement of the movement member and obtains the manipulation signal of the joystick.

8. The electric joystick mechanism according to claim 7, wherein the control unit detects movement velocity of the movement member.

* * * * *